(12) United States Patent
Stephens et al.

(10) Patent No.: US 6,283,132 B1
(45) Date of Patent: Sep. 4, 2001

(54) ANESTHESIA SPIROMETER ABSORBER CIRCUIT CLEANER AND METHOD

(76) Inventors: Roger D. Stephens, 141 Wellesley Crescent, #303, Redwood City, CA (US) 94062; Erwin Schmidmeister, 82 Loyola Ave., Menlo Park, CA (US) 94025

( * ) Notice: Subject to any disclaimer, the term of this patent is extended or adjusted under 35 U.S.C. 154(b) by 0 days.

(21) Appl. No.: 09/435,201

(22) Filed: Nov. 5, 1999

(51) Int. Cl.[7] .................................. B08B 9/00; B08B 3/00
(52) U.S. Cl. ................. 134/22.1; 134/102.3; 134/166 R; 134/168 R
(58) Field of Search ............................... 134/22.1, 102.3, 134/166 R, 168 R, 171

(56) References Cited

U.S. PATENT DOCUMENTS

| | | | |
|---|---|---|---|
| 4,354,514 | * 10/1982 | Sundheimer et al. | 134/152 |
| 4,941,493 | * 7/1990 | Wieringa | 134/166 R |
| 4,971,087 | * 11/1990 | Benedetti et al. | 134/104.1 |
| 5,415,192 | * 5/1995 | Pera | 134/104.1 |

* cited by examiner

*Primary Examiner*—Randy Gulakowski
*Assistant Examiner*—Yolanda E. Wilkins
(74) *Attorney, Agent, or Firm*—Peninsula IP Group; Douglas A. Chaikin; Finn T. Simmensen

(57) ABSTRACT

Disclosed for cleaning an anesthesia spirometry absorber circuit is a cleaning and drying apparatus which includes an adapter for introducing fluids into the exhalation valve after the exhalation valve dome has been removed, a proportionating disk, to be inserted in place of the prior art exhalation valve disk, for directing fluids from the exhalation valve simultaneously into the spirometry valve and into the spigot end of the exhalation valve, a shunt for connecting the exhalation valve spigot end to the inhalation valve spigot end, and a collector for gathering fluids exiting from the spirometry valve and inhalation valve. The collector is insertable between the top cap and bottom cap in place of the removable absorbent canisters of the absorber circuit. An air blower-heater is disclosed for introducing air into the adapter to dry the absorber circuit. The air blower-heater is configured to rest within and to be supported by the adapter, which is securely attachable atop the exhalation valve.

11 Claims, 3 Drawing Sheets

ANESTHESIA SPIROMETER ABSORBER CIRCUIT CLEANER AND METHOD

BACKGROUND OF THE INVENTION

1. Field of the Invention

This invention relates generally to anesthesia ventilation systems, more particularly to anesthesia spirometer and circle absorption circuits, and especially to cleaning such circuits.

2. Background

In a modern medical clinical setting, it is frequently necessary to assist and control the breathing of a patient who is unable to breathe independently. The anesthesia ventilation systems used for this purpose commonly include a device known as an anesthesia circle absorption system. The patient breathes through this device. When inhaling, the patient draws gases from the closed circle absorption system through a breathing circuit via a unidirectional inhalation valve. When the patient exhales, the inhalation valve closes and an exhalation valve, which was closed during inhalation, opens. The exhaled gases pass through the exhalation valve and into absorbent canisters where carbon dioxide is removed from the exhaled gases.

Because the patient s breath includes a mixture of water vapor and biological matter possibly including pathogens, the absorber circuit must be cleaned and dried in order to remain sanitary. Sanitation has taken on renewed importance after several recent and alarming reports of the detection of antibiotic-resistant bacteria in medical facilities.

Cleaning and drying should be completed before the circuit is used again. As a practical matter, this should be done quickly in order to minimize the time the circuit is out of service. Generally, the absorbent canisters are also replaced before the next use. Thus, efficiency and convenience favor cleaning the circuit at that time rather than waiting until later or leaving the circuit disassembled. It is also preferable for practical reasons to accomplish these tasks in or near the operating room rather than transporting the circuit to a remote cleaning facility. It is also desirable to avoid the inconvenience of immersing the whole circuit in a cleaning tank, although certain components may be removed and dealt with separately. What is needed is an efficient, rapid way of cleaning and drying the absorber circuit without transporting it to a remote location and without providing a cleaning tank in which to immerse the circuit. What is especially needed is a way of doing so which is performed locally and does not require expensive cleaning facilities.

SUMMARY OF THE INVENTION

It is an object of the present invention to clean and dry a circle absorption system spirometry absorber circuit.

It is an additional object of the present invention to clean and dry the circuit quickly and efficiently and, in particular, to do so shortly after using the circuit and without transporting the circuit far from the place where it was used.

It is an additional object of the present invention to clean and dry the spirometry absorber circuit without the need of expensive permanent facilities such as an immersion tank.

It is an additional object of the present invention to provide a compact, inexpensive apparatus for such cleaning and, in particular, to provide such an apparatus which makes efficient use of the configuration of a widely used type of spirometry absorber circuit.

In accordance with the above objects and those that will be mentioned and will become apparent below, for cleaning and drying an absorber circuit where the absorber circuit includes an inhalation valve, an exhalation valve, a spirometry valve and a means for receiving removable absorbent canisters located beneath the spirometry valve, a circuit cleaning apparatus according to the present invention comprises:

a shunt for establishing a fluid path from the exhalation valve of the absorber circuit to the inhalation valve thereof, the shunt comprising a first end connectable to the spigot end of the exhalation valve and a second end connectable to the spigot end of the inhalation valve, an adapter for introducing a fluid into the exhalation valve of the absorber circuit, the adapter comprising an upper orifice, a lower orifice adapted for connection to the exhalation valve of the absorber circuit, and a conical-shaped body therebetween;

a proportionating disk insertable within the exhalation valve body for splitting a fluid stream entering the exhalation valve body from the adapter, the proportionating disk splitting the fluid stream into a first path exiting the exhalation valve body and entering the absorber circuit spirometry valve and a second path exiting the spigot end of the exhalation valve;

a collector for collecting a liquid exiting from the absorber circuit spirometry valve, the collector being insertable into the absorber circuit in place of the removable absorbent canisters thereof, the collector having a separator and a side portion, the separator and side portion defining a liquid collecting chamber, the side portion defining an orifice so positioned as to receive liquid exiting from the absorber circuit spirometry valve while providing a path for air to escape between the side portion and the top cap of the absorber circuit; and an air heating and blowing device for introducing heated air into the adapter, the air heating and blowing device comprising an air outlet adapted to engage the upper orifice and rest within the conical shaped body of the adapter, whereby both the inhalation and exhalation circuits of the absorber circuit are rinsable and air-dryable without immersion of the absorber circuit in cleaning solution.

In an exemplary embodiment of a circuit cleaning apparatus according to the present invention, the connector is a hose, the adapter includes a ring nut and the proportionating disk is circular and defines a fluid-channeling opening. The proportionating disk is formed from a ceramic material.

In another exemplary embodiment of a circuit cleaning apparatus according to the present invention, a handle projects from the collector to facilitate installation and removal of the collector.

In a preferred embodiment of a circuit cleaning apparatus according to the present invention, the bottom of the collector includes an air relief opening.

Also in accordance with the above objects and those that will become apparent below, a method for cleaning and drying an anesthesia spirometry absorber circuit, where the absorber circuit includes an inhalation valve, an exhalation valve, a spirometry valve and a means for receiving removable absorbent canisters located beneath the spirometry valve, comprises the steps of: providing:

a shunt for establishing a fluid path from the exhalation valve of the absorber circuit to the inhalation valve thereof, the shunt comprising a first end connectable to the spigot end of the exhalation valve and a second end connectable to the spigot end of the inhalation valve;

an adapter for introducing a fluid into the exhalation valve of the absorber circuit, the adapter comprising an upper orifice, a lower orifice adapted for connection to the exhalation valve of the absorber circuit, and a conical-shaped body therebetween;

a proportionating disk insertable within the exhalation valve body for splitting a fluid stream entering the exhalation valve body from the adapter, the proportionating disk splitting the fluid stream into a first path exiting the exhalation valve body and entering the absorber circuit spirometry valve and a second path exiting the spigot end of the exhalation valve;

a collector for collecting a liquid exiting from the absorber circuit spirometry valve, the collector being insertable into the absorber circuit in place of the removable absorbent canisters thereof, the collector having a separator and a side portion, the separator and side portion defining a liquid collecting chamber, the side portion defining an orifice so positioned as to receive liquid exiting from the absorber circuit spirometry valve while providing a path for air to escape between the side portion and the top cap of the absorber circuit; and an air heating and blowing device for introducing heated air into the adapter, the air heating and blowing device comprising an air outlet adapted to engage the upper orifice and rest within the conical shaped body of the adapter, connecting the shunt between the spigot ends of the exhalation and inhalation valves;

removing the exhalation valve dome and the exhalation valve disk, inserting the proportionating disk in place of the exhalation valve disk, and securing the adapter lower end to the exhalation valve upper orifice;

removing the absorbent canisters from the absorber circuit and inserting the collector in place thereof;

introducing a cleaning liquid into the adapter and allowing the liquid to flow through the absorber circuit; and fluidly connecting the air heating and blowing device to the adapter upper orifice and operating the air heating and blowing device until the absorber circuit is dry.

In an example of this method, the air is introduced into the circuit at approximately 46 degrees Centigrade. In another example, the cleaning fluid is sterile water. In a preferred example, the volume of cleaning fluid is approximately one liter.

Also in accordance with the above objects and those that will be mentioned and will become apparent below, a circuit cleaning apparatus, for cleaning and drying an anesthesia spirometry absorber circuit where the absorber circuit includes an inhalation valve, an exhalation valve including a body and spigot end, and a spirometry valve positioned beneath the exhalation valve body, comprises:

a shunt for establishing a fluid path from the spigot end of the exhalation valve of the absorber circuit into the inhalation valve thereof;

an adapter, capable of fluid-tight coupling to the exhalation valve, for introducing a fluid therein;

a proportionating disk, insertable within the exhalation valve, for splitting a fluid stream entering the exhalation valve body from the adapter, the proportionating disk being capable, when so inserted, of splitting the fluid stream into a first path exiting the exhalation valve body and entering the absorber circuit spirometry valve and a second path exiting the spigot end of the exhalation valve; and a collector for collecting a liquid exiting from the absorber circuit spirometry valve, the collector being capable of receiving a liquid stream exiting the spirometry valve under gravity, whereby both the inhalation and exhalation circuits of the absorber circuit are cleanable without immersion of the absorber circuit.

It is an advantage of the present invention that gravity is sufficient to deliver a cleaning fluid through both paths of the absorber circuit, eliminating the need to submerge the entire absorber circuit in a cleaning bath. It is an additional advantage of the present invention that efficient use is made of the configuration of a common type of anesthesia absorber circuit.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein.

DETAILED DESCRIPTION OF THE INVENTION

By way of introduction, the prior art absorber circuit of FIG. 1 will be described. The present invention will then be described with reference to FIG. 2, an exemplary embodiment of the circuit cleaning apparatus according to the present invention as installed on a spirometry absorber circuit of the type shown in FIG. 1.

Figure 1:
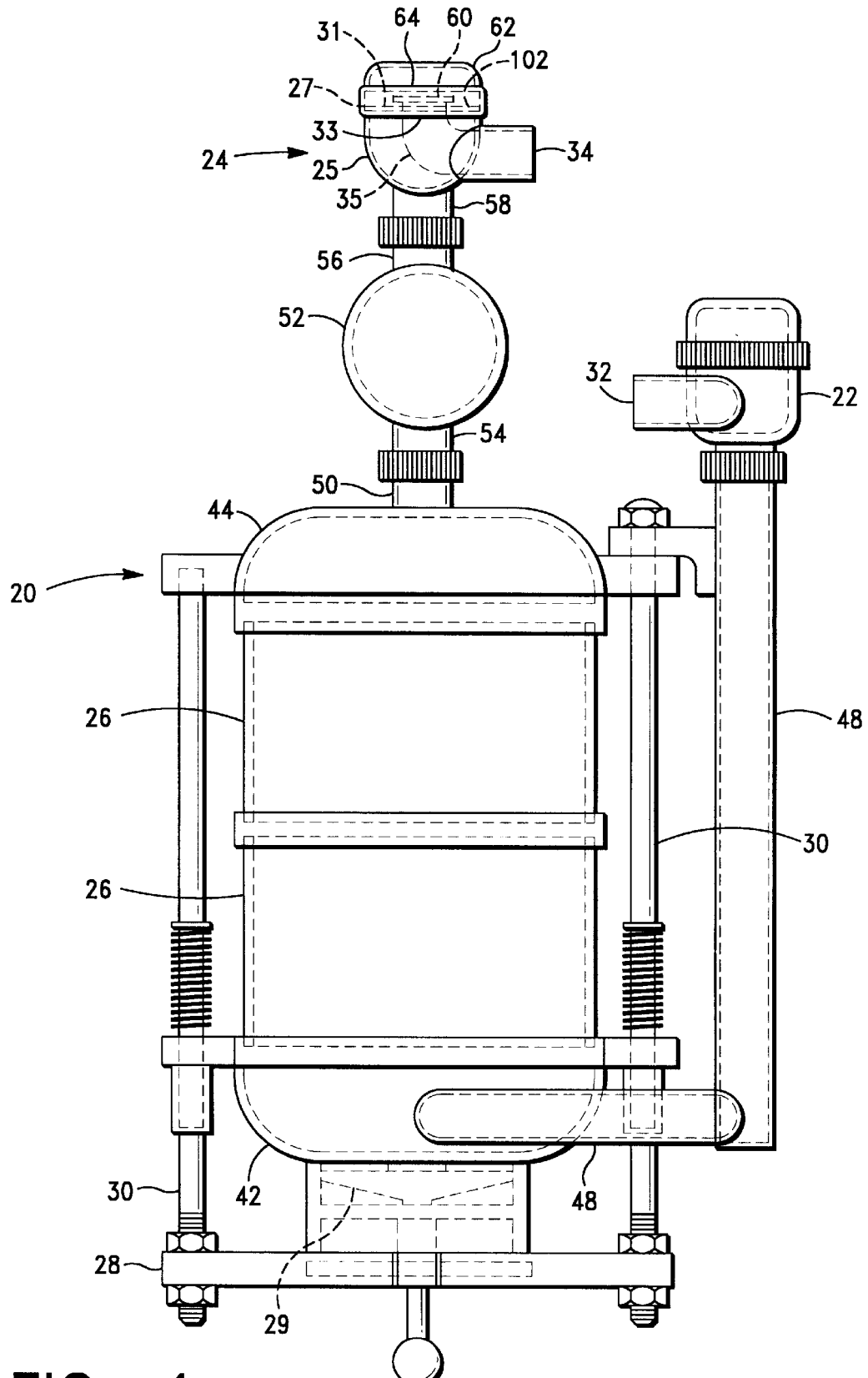
FIG. 1 is a side view of a prior art anesthesia spirometry absorber circuit.

FIG. 1 illustrates a prior art anesthesia spirometry absorber circuit (hereinafter referred to as the absorber circuit), shown generally at 20. Such an absorber circuit typically includes an inhalation valve 22 and an exhalation valve 24, both of which fluidly communicate with a gas source and with the patient's airway. Functionally, the inhalation valve 22 establishes a path for one-way gas flow from a source of anesthesia gases into a patient's airway and the exhalation valve 24 establishes a path for one-way gas flow from the patient's airway to one or more absorbent canisters 26. Together, the gas source, inhalation and exhalation valves 22 and 24 and absorbent canisters 26 provide a means of controlling the gases breathed by the patient and of channeling those gases so that their pressure, volume, flow rate and composition can be measured.

Structurally, such an absorber circuit 20 includes a base 28 and a frame 30 supported by the base 28. A round bottom cap 42 is supported by the frame 30. The inhalation valve 22 is supported by the frame 30 and the bottom cap 42. The inhalation valve 22 includes an inhalation spigot end 32. A round top cap 44 is supported by the frame 30. Together, the top cap 44 and bottom cap 42 sealingly engage one or more absorbent canisters 26 which are insertable within the frame 30 and between the top cap 44 and the bottom cap 42. The base 28 includes a removable dust cup 29. An inhalation valve pipe 48 leads from the inhalation valve 22 to the bottom cap 42.

The uppermost portion of the top cap 44 defines a centrally positioned top cap connector 50. A spirometry valve 52 is located immediately above the top cap connector 50. The spirometry valve 52 includes a tubular lower spirometry valve connector 54 and a tubular upper spirometry valve connector 56. The top cap connector 50 supports the lower spirometry valve connector 54 and fluidly connects the lower spirometry valve connector 54 to the absorbent canisters 26.

The exhalation valve 24 includes a bowl 25 which has a threaded circular outer periphery 27 and a spigot end 34. A valve plate 31 extends horizontally across the bowl at the level of the outer periphery 27. The valve plate 31 defines a central orifice 33 to which is attached a short pipe 35 which fluidly communicates with the exhalation valve spigot end 34. The valve plate 31 forms six annularly arranged openings 102, each approximately 3/16 by 5/16 inch, proximate the outer periphery 27. The valve plate 31 also forms six annularly arranged upwardly projecting studs 108, each approximately four millimeters in height. For normal operation, an exhalation valve disk 60, having diameter approximately two inches and thickness approximately one or two millimeters, rests between the studs 108 on top of the valve plate 31.

An exhalation valve dome 62 sits on top of the outer periphery 27 and covers the bowl 25. The dome 62 defines six annularly arranged downwardly projecting studs (not shown) comparable to the studs 108 of the valve plate 31. When the dome 62 is positioned on top of the outer periphery 27 of exhalation valve 24, the exhalation valve.

Figure 2:
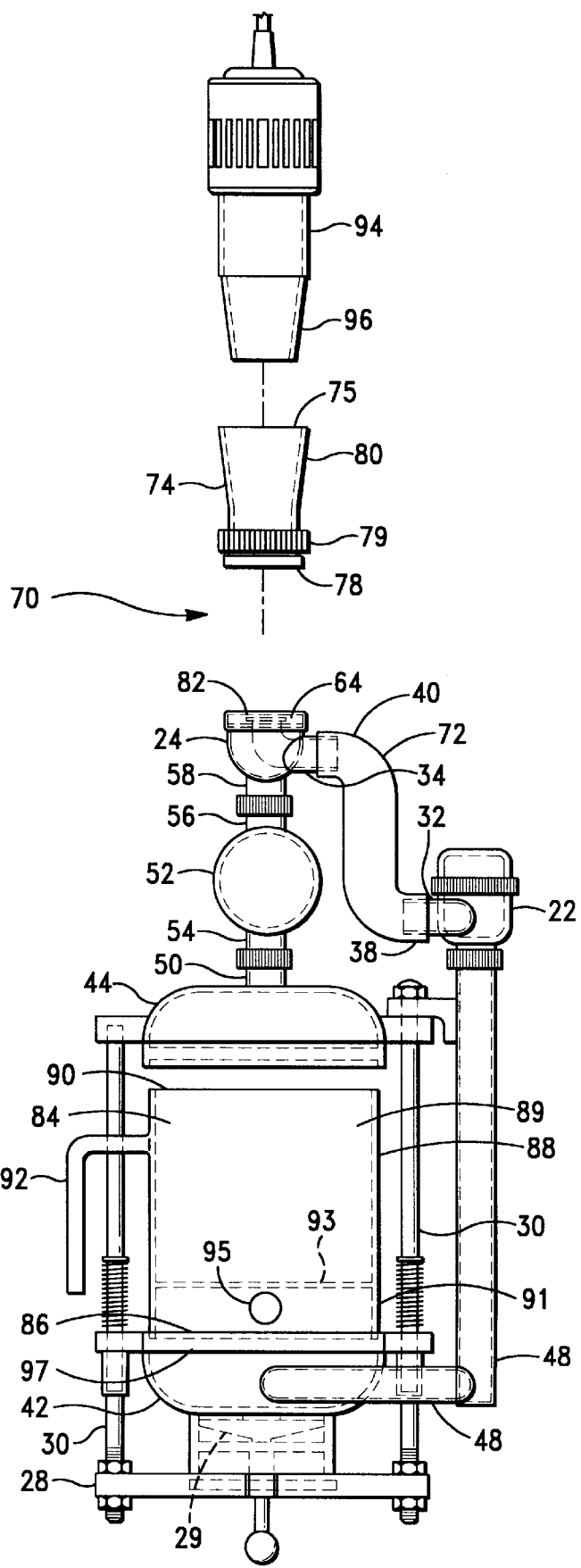
FIG. 2 is a side view of an exemplary embodiment of the circuit cleaning apparatus according to the present invention as installed on an absorber circuit of the type shown in FIG. 1.

The present invention will now be described with reference to FIG. 2, which shows the circuit cleaning apparatus 70 of the present invention installed on an absorber circuit of the type illustrated in FIG. 1. The circuit cleaning apparatus 70 includes a shunt 72 having a first end 38 fluidly connectable to the inhalation valve spigot end 32 and a second end 40 fluidly connectable to the exhalation valve spigot end 34. The circuit cleaning apparatus 70 includes an adapter 74 for introducing a fluid into the exhalation valve 24. The adapter 74 includes an adapter upper end 76, an adapter lower end 78 and a conical body 80 therebetween. The adapter lower end 78 is adapted to fluidly connect the adapter 74 to the exhalation valve upper orifice 64. In an exemplary embodiment of the circuit cleaning apparatus 70 of the present invention, the adapter lower end 78 includes a ring nut 79 for securely coupling the adapter lower end 78 to the exhalation valve upper orifice 64.

Figure 3:
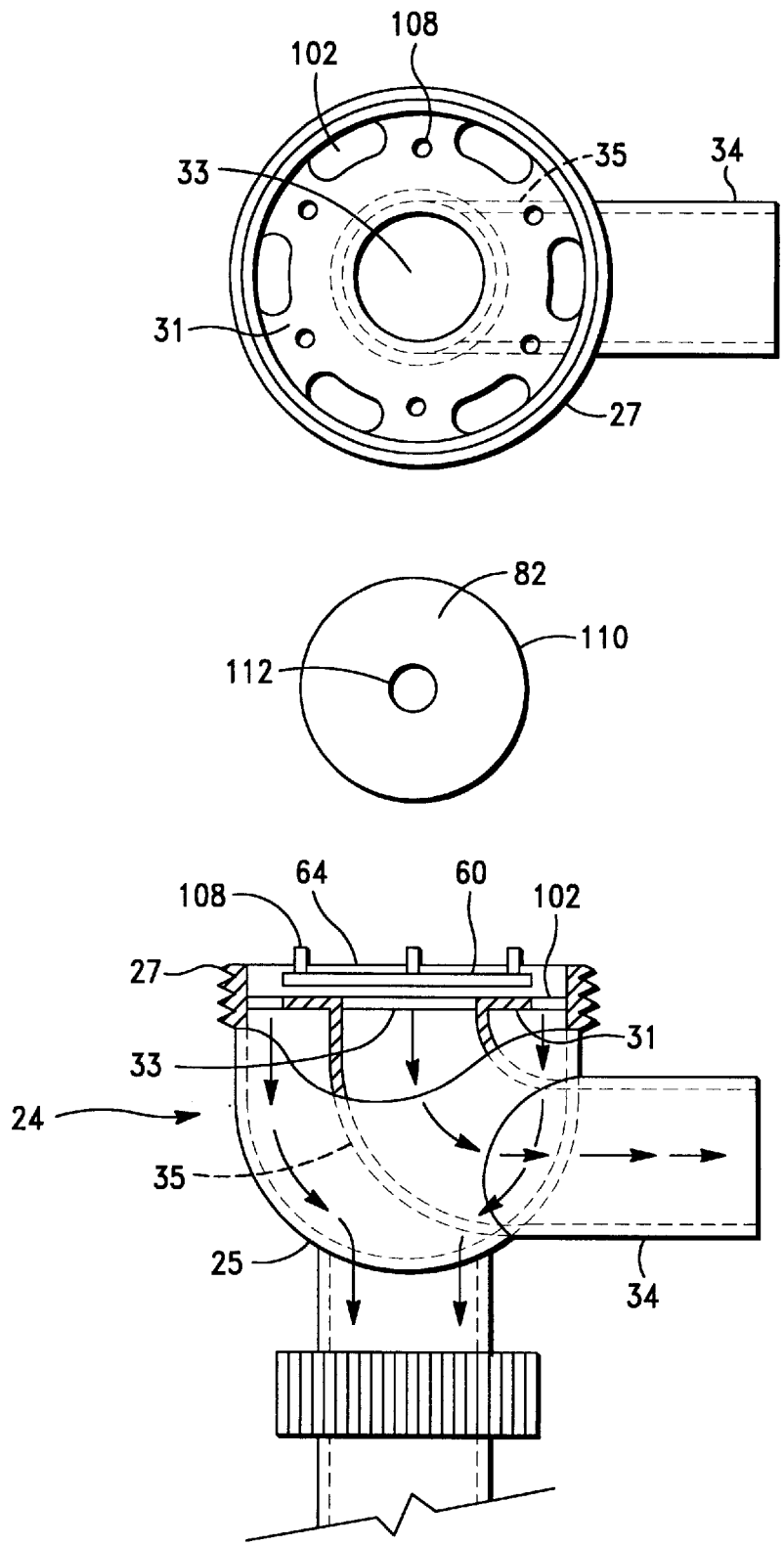
FIG. 3 is a magnified side view of the proportionating disk of an exemplary embodiment of the circuit cleaning apparatus according to the present invention as it is to be installed in place of the valve disk of the exhalation valve of an absorber circuit of the type shown in FIG. 1.

With reference again to FIG. 2 and now also to FIG. 3, the circuit cleaning apparatus 70 includes a proportionating disk 82. The proportionating disk 82 is inserted in the exhalation valve 24 in place of the exhalation valve disk 60 that would normally rest between the studs 108. The proportionating disk 82 is capable of splitting a fluid stream entering the exhalation valve upper orifice 64 into two fluid paths. The first path exits the exhalation valve lower connector 58, enters the spirometry valve upper connector 56, and passes through the spirometry valve 52, spirometry valve lower connector 54, top cap connector 50 and top cap 44. The second path exits the exhalation valve spigot end 34 and passes through the shunt 72, inhalation valve spigot end 32, inhalation valve 22 and inhalation valve pipe 48 through the bottom cap 42 into the dust cup 29. Thus, both parts of the absorber circuit are flushed. In an exemplary embodiment of the circuit cleaning apparatus 70 according to the present invention, the proportionating disk 82 is shaped to split a stream of cleaning fluid when the fluid is introduced through the adapter 74.

FIG. 3 shows the proportionating disk 82, which comprises a ceramic material and is circular in shape. After the dome 62 and exhalation valve disk 60 are removed, the proportionating disk 82 is placed between the studs 108 of the valve plate 31. The proportionating disk 82 has a thickness of approximately 1 millimeter, a circular outer edge 110 defining a diameter of approximately 1¼ inch, and a central opening 112 with a diameter of approximately ¼ inch. During cleaning, when liquid is introduced into the exhalation valve, the proportionating disk 82 sufficiently restricts the exit of liquid via the exhalation valve spigot end 34 that only approximately 10% of the liquid passes through the central opening 112 of the proportionating disk 82 while the remaining 90% passes through the openings 102 into the spirometry valve 52.

The circuit cleaning apparatus 70 includes a collector 84 for collecting the liquid as it exits from the spirometry valve lower connector 54. The collector 84 is sized and shaped to fit within the frame 30 of the absorber circuit 20 after the absorbent canisters 26 have been removed. The collector 84 has an open bottom 86 which rests on the bottom cap 42. The collector 84 has a side portion 88 and a separator 93. The separator 93 and side portion 88 define a liquid collecting chamber 89 above the separator 93. The side portion 88 defines an open upper end 90 positioned to receive liquid exiting through the top cap 44. The side portion 88 is short enough that when the collector 84 is installed, the upper end 90 is spaced apart from the top cap 44 so as to provide a path for displaced air to escape between the side portion 88 and the top cap 44. Beneath the separator 93, the side portion 88 of the collector 84 includes a lower side portion 91 defining an open lower end 97 and a round air relief opening 95.

In an exemplary embodiment of the circuit cleaning apparatus 70 according to the present invention, the collector 84 has the shape of a cylindrical cup. In preferred embodiment, the side portion 88 of the collector 84 defines a handle 92.

The circuit cleaning apparatus 70 includes an air heating and blowing device 94 for introducing heated air into the adapter 74. The air heating and blowing device 94 comprises an air outlet 96 adapted to engage the adapter upper end 76 and to rest within the conical adapter body 80. In an exemplary embodiment of the circuit cleaning apparatus 70 according to the present invention, the air heating and blowing device 94 includes an electric motor-driven blower and an electric resistive heating element.

In operation, the shunt 72 is attached between the spigot ends 32 and 34 of the inhalation valve 22 and exhalation valve 24. The collector 84 is placed beneath the spirometry valve in place of the absorbent canisters 26, which have been removed. Thus, while in use, the collector 84 requires no additional space adjacent the absorber circuit. The exhalation valve dome 62 is removed from the exhalation valve 24. The proportionating disk 82 is inserted in place of the exhalation valve disk 60, which has been removed. The adapter 74 is mounted atop the exhalation valve upper orifice 64. An appropriate volume of a liquid is poured into the adapter 74, whereupon the proportionating disk 82 splits the liquid stream so that approximately 90% passes through the above described first path and into the collector 84 while the remainder passes through the inhalation valve 22 and exits through the inhalation valve pipe 48 and through the bottom cap 42 into the dust cup 29. In an exemplary embodiment of an absorber circuit cleaning apparatus according to the present invention, the proportionating disk 82 is configured such that one liter of liquid flows through the circuit in the above-described manner in approximately 15 seconds.

Although the absorber circuit may be left wet after cleaning, it is preferable to dry the absorber circuit in a timely manner to reduce the likelihood of contamination and to make the circuit ready for use as early as possible. Therefore, the present invention contemplates the optional, although highly recommended, step of drying the circuit immediately after cleaning. To dry the absorber circuit 20, the air heating and blowing device 94 is placed atop and into the adapter and operated for a duration of approximately three to five minutes. The proportionating disk 82 splits the air stream so that both parts of the absorber circuit 20 are dried. Air which passes through the spirometry valve 52 exits the top cap connector into the top cap 44 and escapes above the open upper end 90 of the collector 84. Air which passes through the inhalation valve pipe 48 into the bottom cap 42 exits through the air relief opening 95 in the lower side portion 91 of the collector 84. In an exemplary method of cleaning an absorber circuit according to the present invention, air is delivered from the air heating and blowing device 94 at a temperature of 46 degrees Centigrade and a rate of 2 liters per minute.

The present invention takes advantage of the fact that the exhalation valve 24, which includes the exhalation spigot end 34, is positioned above the level of the inhalation valve 22, which includes the inhalation spigot end 32. In particular, the present invention exploits gravity to deliver cleaning fluid through both paths of the absorber circuit. The present invention additionally takes advantage of the fact that the exhalation valve dome 62 is easily removed to provide access to the exhalation valve disk 60. Finally, the present invention takes advantage of the fact that when the absorbent canisters 26 are removed from beneath the top cap 44, an open space is made available. In particular the present invention exploits this open space for collecting the cleaning fluid from the absorber circuit.

While the foregoing detailed description sets forth several embodiments of the circuit cleaning apparatus in accordance with this invention, it is to be understood that the above description is illustrative only and not limiting of the disclosed invention. The invention is to be limited only by the claims as set forth below.

What is claimed is:

1. A circuit cleaning apparatus for cleaning and drying an anesthesia spirometry absorber circuit where the absorber circuit includes an inhalation valve, an exhalation valve, a spirometry valve and a means for receiving removable absorbent canisters located beneath the spirometry valve, the circuit cleaning apparatus comprising:

a shunt for establishing a fluid path from the exhalation valve of the absorber circuit to the inhalation valve thereof, the connector comprising a first end connectable to the spigot end of the exhalation valve and a second end connectable to the spigot end of the inhalation valve;

an adapter for introducing a fluid into the exhalation valve of the absorber circuit, the adapter comprising an upper orifice, a lower orifice adapted for connection to the exhalation valve of the absorber circuit, and a conical-shaped body therebetween;

a proportionating disk insertable within the exhalation valve body for splitting a fluid stream entering the exhalation valve body from the adapter, the proportionating disk splitting the fluid stream into a first path exiting the exhalation valve body and entering the absorber circuit spirometry valve and a second path exiting the spigot end of the exhalation valve;

a collector for collecting a liquid exiting from the absorber circuit spirometry valve, the collector being insertable into the absorber circuit in place of the removable absorbent canisters thereof, the collector having a separator and a side portion, the separator and side portion defining a liquid collecting chamber, the side portion defining an orifice so positioned as to receive liquid exiting from the absorber circuit spirometry valve while providing a path for air to escape between the side portion and the top cap of the absorber circuit; and an air heating and blowing device for introducing heated air into the adapter, the air heating and blowing device comprising an air outlet adapted to engage the upper orifice and rest within the conical shaped body of the adapter, whereby both the inhalation and exhalation circuits of the absorber circuit are rinsable and air-dryable without immersion of the absorber circuit.

2. A circuit cleaning apparatus as set forth in claim 1, wherein the circuit includes a bottom cap and an inhalation valve pipe establishing a fluid path from the inhalation valve to the bottom cap;

the collector includes a separator, the separator defines a space above the bottom cap, the space fluidly communicating with the inhalation valve pipe; and the side portion of the collector defines an air relief opening through which air exiting the inhalation valve pipe escapes the space above the bottom cap.

3. A circuit cleaning apparatus as set forth in claim 1, wherein a handle projects from the side portion of the collector.

4. A circuit cleaning apparatus as set forth in claim 2, wherein a handle projects from the side portion of the collector.

5. A method for cleaning an anesthesia spirometry absorber circuit where the absorber circuit includes an inhalation valve, an exhalation valve, a spirometry valve and a means for receiving removable absorbent canisters located beneath the spirometry valve, the method comprising the steps of:

providing:

a shunt for establishing a fluid path from the exhalation valve of the absorber circuit to the inhalation valve thereof, the connector comprising a first end connectable to the spigot end of the exhalation valve and a second end connectable to the spigot end of the inhalation valve;

an adapter for introducing a fluid into the exhalation valve of the absorber circuit, the adapter comprising an upper orifice, a lower orifice adapted for connection to the exhalation valve of the absorber circuit, and a conical-shaped body therebetween;

a proportionating disk insertable within the exhalation valve body for splitting a fluid stream entering the exhalation valve body from the adapter, the proportionating disk splitting the fluid stream into a first path exiting the exhalation valve body and entering the absorber circuit spirometry valve and a second path exiting the spigot end of the exhalation valve; and a collector for collecting a liquid exiting from the absorber circuit spirometry valve, the collector being insertable into the absorber circuit in place of the removable absorbent canisters thereof, the collector having a separator and a side portion, the separator and side portion defining a liquid collecting chamber, the side portion defining an orifice so positioned as to receive liquid exiting from the absorber circuit spirometry valve while providing a path for air to escape between the side portion and the top cap of the absorber circuit;

connecting the shunt between the spigot ends of the exhalation and inhalation valves;

removing the exhalation valve dome, removing the exhalation valve disk from the exhalation valve, inserting the proportionating disk in place thereof, and securing the adapter lower end to the exhalation valve upper orifice;

removing the absorbent canisters from the absorber circuit and inserting the collector in place thereof; and introducing a cleaning liquid into the adapter and allowing the liquid to flow through the absorber circuit.

6. A method as set forth in claim 5, comprising the additional steps of:

providing an air heating and blowing device for introducing heated air into the adapter, the air heating and blowing device comprising an air outlet adapted to engage the upper orifice and rest within the conical shaped body of the adapter; and fluidly connecting the air heating and blowing device to the adapter upper orifice and operating the air heating and blowing device until the absorber circuit is dry.

7. A method as set forth in claim 5, wherein the cleaning liquid is sterile water.

8. A method as set forth in claim 5, wherein the cleaning liquid is approximately one liter in volume.

9. A method as set forth in claim 5, wherein the air is introduced into the absorber circuit at a temperature of approximately 46 degrees Centigrade.

10. A method as set forth in claim 5, wherein the air is introduced into the absorber circuit at a rate of approximately 2 liters per minute.

11. A circuit cleaning apparatus for cleaning and drying an anesthesia spirometry absorber circuit where the absorber circuit includes an inhalation valve, an exhalation valve including a body and spigot end, and a spirometry valve positioned beneath the inhalation valve body, the circuit cleaning apparatus comprising:

a shunt for establishing a fluid path from the spigot end of the exhalation valve of the absorber circuit into the inhalation valve thereof;

an adapter, capable of fluid-tight coupling to the exhalation valve, for introducing a fluid therein;

a proportionating disk, insertable within the exhalation valve, for splitting a fluid stream entering the exhalation valve body from the adapter, the proportionating disk being capable, when so inserted, of splitting the fluid stream into a first path exiting the exhalation valve body and entering the absorber circuit spirometry valve and a second path exiting the spigot end of the exhalation valve; and a collector for collecting a liquid exiting from the absorber circuit spirometry valve, the collector being capable of receiving the liquid stream exiting the spirometry valve under gravity, whereby both the inhalation and exhalation circuits of the absorber circuit are cleanable without immersion of the absorber circuit.

* * * * *